(12) United States Patent
Kusnoto et al.

(10) Patent No.: US 10,878,954 B2
(45) Date of Patent: Dec. 29, 2020

(54) DENTO-CRANIOFACIAL CLINICAL COGNITIVE DIAGNOSIS AND TREATMENT SYSTEM AND METHOD

(71) Applicants: Budi Kusnoto, Chicago, IL (US); Ahmed Kaboudan, Cairo (EG); Christoph Peter Bourauel, Bonn (DE); Sameh Mohamed Talaat Taha Mohamed, Cairo (EG)

(72) Inventors: Budi Kusnoto, Chicago, IL (US); Ahmed Kaboudan, Cairo (EG); Christoph Peter Bourauel, Bonn (DE); Sameh Mohamed Talaat Taha Mohamed, Cairo (EG)

(73) Assignee: DIGIBRAIN4, INC., Lake Zurich, IL (US)

( * ) Notice: Subject to any disclaimer, the term of this patent is extended or adjusted under 35 U.S.C. 154(b) by 87 days.

(21) Appl. No.: 16/354,446

(22) Filed: Mar. 15, 2019

(65) Prior Publication Data

US 2019/0295710 A1 Sep. 26, 2019

Related U.S. Application Data

(60) Provisional application No. 62/648,284, filed on Mar. 26, 2018.

(51) Int. Cl.
*G06K 9/00* (2006.01)
*G16H 30/40* (2018.01)
(Continued)

(52) U.S. Cl.
CPC .............. *G16H 30/40* (2018.01); *A61B 6/14* (2013.01); *A61B 6/5217* (2013.01);
(Continued)

(58) Field of Classification Search
CPC ........ G16H 20/00; G16H 20/40; G16H 30/40; G16H 30/20; G16H 10/60; G16H 15/00; G16H 50/30; G16H 50/20; G16H 50/70; G06F 16/352; G06F 16/2465; G06F 16/9535; G06F 19/00; G06F 19/321; G06F 19/32; G06F 19/30; G06F 19/325; G06F 30/00; G06F 2216/03; G06Q 50/24; A61F 2/50; A61F 2007/0017; A61F 2002/30953; G06K 2209/05; G06K 9/6273; G06K 9/6267; G06K 9/00268; G06K 9/00281; G06K 9/00362; G06N 20/00; G06N 20/10;
(Continued)

(56) References Cited

U.S. PATENT DOCUMENTS 10,517,482 B2 * 12/2019 Sato .................. A61B 5/4848
2007/0128574 A1 * 6/2007 Kuo .......................... A61C 7/00
433/24

(Continued)

FOREIGN PATENT DOCUMENTS

WO WO-2019178617 A1 * 9/2019 ........... G06T 7/0012

*Primary Examiner* — Jose L Couso
(74) *Attorney, Agent, or Firm* — Justin Lampel

(57) ABSTRACT

This present system and method provide artificial intelligence systems and methods for automatic identification, localization, recognition, understanding, labelling, analyzing, assessing, deciding and planning related to dento-craniofacial visual assets ('DCVA') for creating a report for patient treatment and consultation.

11 Claims, 17 Drawing Sheets

(51) Int. Cl.
*G06F 16/532* (2019.01)
*G16H 10/60* (2018.01)
*G16H 15/00* (2018.01)
*A61B 6/14* (2006.01)
*A61B 6/00* (2006.01)
*G06T 7/00* (2017.01)

(52) U.S. Cl.
CPC .......... *A61B 6/5294* (2013.01); *G06F 16/532* (2019.01); *G06T 7/0012* (2013.01); *G16H 10/60* (2018.01); *G16H 15/00* (2018.01); *G06T 2207/10116* (2013.01); *G06T 2207/30036* (2013.01)

(58) Field of Classification Search
CPC .. G06N 3/02; G06N 3/08; G06N 5/02; G06N 5/003; G06N 7/005; A61B 6/14; A61B 6/5294; A61B 6/5217; A61B 6/501; A61B 6/463; A61B 6/563; A61B 6/465; A61B 1/00009; A61B 1/0005; A61B 8/463; A61B 8/465; A61B 8/565; A61B 5/0088; A61B 5/4547; A61B 5/4542; A61B 34/10; G06T 7/0012; G06T 7/75; G06T 19/00; G06T 19/20; G06T 17/00; G06T 11/008; G06T 2207/10116; G06T 2207/30036; G06T 2200/04; G06T 2210/04; A61C 7/08; A61C 7/002; A61C 7/00; A61C 7/10; A61C 7/12; A61C 7/145; A61C 7/146; A61C 7/22; A61C 19/063; A61C 19/04; A61C 5/30; A61C 8/0009; A61C 8/009; A61C 8/0093; A61C 9/0046; A61C 9/0086; A61C 9/0053; A61C 9/004; A61C 13/0004; A61C 2007/004

See application file for complete search history.

(56) References Cited

U.S. PATENT DOCUMENTS

| | | | |
|---|---|---|---|
| 2007/0168152 A1* | 7/2007 | Matov | A61C 7/002 702/155 |
| 2007/0238065 A1* | 10/2007 | Sherwood | A61C 7/002 433/24 |
| 2010/0114602 A1* | 5/2010 | Joao | G06Q 50/24 705/2 |
| 2016/0012182 A1* | 1/2016 | Golay | G16H 40/20 705/3 |
| 2016/0048651 A1* | 2/2016 | Papier | G16H 70/60 382/128 |
| 2018/0061054 A1* | 3/2018 | Abraham | A61B 6/501 |
| 2018/0184989 A1* | 7/2018 | Inglese | A61B 6/5217 |
| 2018/0284727 A1* | 10/2018 | Cramer | B29C 64/393 |
| 2019/0231492 A1* | 8/2019 | Sabina | A61B 1/00172 |
| 2019/0269485 A1* | 9/2019 | Elbaz | A61B 5/0059 |
| 2019/0328489 A1* | 10/2019 | Capron-Richard | G06T 7/0012 |

* cited by examiner

| Layer (type) | Output Shape | Param # |
|---|---|---|
| input_1 (InputLayer) | (None, 227, 227, 3) | 0 |
| conv1 (Conv2D) | (None, 113, 113, 64) | 1792 |
| relu_conv1 (Activation) | (None, 113, 113, 64) | 0 |
| pool1 (MaxPooling2D) | (None, 56, 56, 64) | 0 |
| conv2/compress1x1 (Conv2D) | (None, 56, 56, 16) | 1040 |
| conv2/relu_compress1x1 (Activati | (None, 56, 56, 16) | 0 |
| conv2/expand1x1 (Conv2D) | (None, 56, 56, 64) | 1088 |
| conv2/expand3x3 (Conv2D) | (None, 56, 56, 64) | 9280 |
| conv2/relu_expand1x1 (Activatio | (None, 56, 56, 64) | 0 |
| conv2/relu_expand3x3 (Activatio | (None, 56, 56, 64) | 0 |
| conv2/concat (Concatenate) | (None, 56, 56, 128) | 0 |
| conv3/compress1x1 (Conv2D) | (None, 56, 56, 16) | 2064 |
| conv3/relu_compress1x1 (Activati | (None, 56, 56, 16) | 0 |
| conv3/expand1x1 (Conv2D) | (None, 56, 56, 64) | 1088 |
| conv3/expand3x3 (Conv2D) | (None, 56, 56, 64) | 9280 |
| conv3/relu_expand1x1 (Activatio | (None, 56, 56, 64) | 0 |
| conv3/relu_expand3x3 (Activatio | (None, 56, 56, 64) | 0 |
| conv3/concat (Concatenate) | (None, 56, 56, 128) | 0 |
| pool3 (MaxPooling2D) | (None, 27, 27, 128) | 0 |
| conv4/compress1x1 (Conv2D) | (None, 27, 27, 32) | 4128 |
| conv4/relu_compress1x1 (Activati | (None, 27, 27, 32) | 0 |
| conv4/expand1x1 (Conv2D) | (None, 27, 27, 128) | 4224 |

| | | |
|---|---|---|
| conv4/expand3x3 (Conv2D) | (None, 27, 27, 128) | 36992 |
| conv4/relu_expand1x1 (Activatio | (None, 27, 27, 128) | 0 |
| conv4/relu_expand3x3 (Activatio | (None, 27, 27, 128) | 0 |
| conv4/concat (Concatenate) | (None, 27, 27, 256) | 0 |
| conv5/compress1x1 (Conv2D) | (None, 27, 27, 32) | 8224 |
| conv5/relu_compress1x1 (Activati | (None, 27, 27, 32) | 0 |
| conv5/expand1x1 (Conv2D) | (None, 27, 27, 128) | 4224 |
| conv5/expand3x3 (Conv2D) | (None, 27, 27, 128) | 36992 |
| conv5/relu_expand1x1 (Activatio | (None, 27, 27, 128) | 0 |
| conv5/relu_expand3x3 (Activatio | (None, 27, 27, 128) | 0 |
| conv5/concat (Concatenate) | (None, 27, 27, 256) | 0 |
| pool5 (MaxPooling2D) | (None, 13, 13, 256) | 0 |
| conv6/compress1x1 (Conv2D) | (None, 13, 13, 48) | 12336 |
| conv6/relu_compress1x1 (Activati | (None, 13, 13, 48) | 0 |
| conv6/expand1x1 (Conv2D) | (None, 13, 13, 192) | 9408 |
| conv6/expand3x3 (Conv2D) | (None, 13, 13, 192) | 83136 |
| conv6/relu_expand1x1 (Activatio | (None, 13, 13, 192) | 0 |
| conv6/relu_expand3x3 (Activatio | (None, 13, 13, 192) | 0 |
| conv6/concat (Concatenate) | (None, 13, 13, 384) | 0 |
| conv7/compress1x1 (Conv2D) | (None, 13, 13, 48) | 18480 |
| conv7/relu_compress1x1 (Activati | (None, 13, 13, 48) | 0 |
| conv7/expand1x1 (Conv2D) | (None, 13, 13, 192) | 9408 |
| conv7/expand3x3 (Conv2D) | (None, 13, 13, 192) | 83136 |

| | | | |
|---|---|---|---|
| 99 | conv7/relu_expand1x1 (Activatio | (None, 13, 13, 192) | 0 |
| 100 | | | |
| 101 | conv7/relu_expand3x3 (Activatio | (None, 13, 13, 192) | 0 |
| 102 | | | |
| 103 | conv7/concat (Concatenate) | (None, 13, 13, 384) | 0 |
| 104 | | | |
| 105 | | | |
| 106 | conv8/compress1x1 (Conv2D) | (None, 13, 13, 64) | 24640 |
| 107 | | | |
| 108 | conv8/relu_compress1x1 (Activati | (None, 13, 13, 64) | 0 |
| 109 | | | |
| 110 | conv8/expand1x1 (Conv2D) | (None, 13, 13, 256) | 16640 |
| 111 | | | |
| 112 | conv8/expand3x3 (Conv2D) | (None, 13, 13, 256) | 147712 |
| 113 | | | |
| 114 | conv8/relu_expand1x1 (Activatio | (None, 13, 13, 256) | 0 |
| 115 | | | |
| 116 | conv8/relu_expand3x3 (Activatio | (None, 13, 13, 256) | 0 |
| 117 | | | |
| 118 | conv8/concat (Concatenate) | (None, 13, 13, 512) | 0 |
| 119 | | | |
| 120 | | | |
| 121 | conv9/compress1x1 (Conv2D) | (None, 13, 13, 64) | 32832 |
| 122 | | | |
| 123 | conv9/relu_compress1x1 (Activati | (None, 13, 13, 64) | 0 |
| 124 | | | |
| 125 | conv9/expand1x1 (Conv2D) | (None, 13, 13, 256) | 16640 |
| 126 | | | |
| 127 | conv9/expand3x3 (Conv2D) | (None, 13, 13, 256) | 147712 |
| 128 | | | |
| 129 | conv9/relu_expand1x1 (Activatio | (None, 13, 13, 256) | 0 |
| 130 | | | |
| 131 | conv9/relu_expand3x3 (Activatio | (None, 13, 13, 256) | 0 |
| 132 | | | |
| 133 | conv9/concat (Concatenate) | (None, 13, 13, 512) | 0 |
| 134 | | | |
| 135 | | | |
| 136 | drop9 (Dropout) | (None, 13, 13, 512) | 0 |
| 137 | | | |
| 138 | conv10 (Conv2D) | (None, 13, 13, 13) | 6669 |
| 139 | | | |
| 140 | relu_conv10 (Activation) | (None, 13, 13, 13) | 0 |
| 141 | | | |
| 142 | global_average_pooling3d (Globa | (None, 13) | 0 |
| 143 | | | |
| 144 | loss (Activation) | (None, 13) | 0 |
| 145 | | | |

906

FIG. 9    Total params: 729,165

US 10,878,954 B2

DENTO-CRANIOFACIAL CLINICAL COGNITIVE DIAGNOSIS AND TREATMENT SYSTEM AND METHOD

REFERENCE TO RELATED APPLICATIONS

This application claims priority to U.S. Provisional Application No. 62/648,284, which is entitled "METHOD AND SYSTEM FOR AUTOMATICALLY DERIVING QUANTITATIVE DENTO-CRANIOFACIAL DATA" which was filed on Mar. 26, 2018, the entire contents of which are incorporated by reference herein.

TECHNICAL FIELD

The present system and method provide artificial intelligence systems and methods for automatic identification, localization, recognition, understanding, labelling, analyzing, assessing, deciding and creating a report deriving an outcome for patient treatment and consultation related to Dento-Craniofacial Visual Assets ('DCVA') media.

The present DCVA system and method may be capable of automatic identification, understanding, localization, recognition, labelling and metadata generation of DCVA, including anatomical modifiers like upper and lower, right side and left side for creating a report for patient treatment and consultation.

Further, the DCVA present system and method may be capable of recognizing and rejecting non-relevant dento-craniofacial visual assets for creating a report for patient treatment and consultation.

Even further, the present DCVA system and method also may utilize a unique artificial intelligence search engine capable of accurately recognizing and picking a correct dento-craniofacial visual assets from large repositories for creating a report for patient treatment and consultation.

The present DCVA system and method may also utilize a unique artificial intelligence system, "DCVA Classifier", capable of auto-labelling and auto-generating of metadata and persisting the results in query-friendly formats, like RDBMS and noSQL databases and structured text formats for creating a report for patient treatment and consultation. The reports may be printed physical reports in an embodiment. The data may further be used to teach other artificial intelligence systems.

Further, the present DCVA system and method may also utilize a unique artificial intelligence search engine filter called a "DCVA Search Engine Booster Filter" which may be capable of filtering and boosting the efficiency of the results returned from other World Wide Web search engines, such as Google®. Assets matching the searched terms are selected, while all other non-relevant to the searched terms are discarded. The results may be used for creating a report deriving an outcome for patient treatment and consultation.

Still further, the present DCVA system and method may utilize a unique artificial intelligence system called a "Dental Insurance Treatment Auto-Authorizer" which may be capable of auto-generation of dental-insurance treatment authorization, by auto-generation of a Handicapping Labio-Lingual Deviation Index (HLD) score report, by automatic identification, localization, recognition, understanding, analyzing, and assessing quantitively and qualitatively a patient's multiple DCVA for creating a report for patient treatment and consultation.

And, the present DCVA system and method may utilize a unique artificial intelligence system called a "Landmarks Localizer" which may be capable of auto-identification and localization of dento-craniofacial landmarks, including performing quantitative analysis based on landmarks coordinates and relative positions for creating a report for patient treatment and consultation. The reports may be physical reports in an embodiment.

The present DCVA system and method may also utilize a unique artificial intelligence system called an "Ectopic Eruption Discoverer" which may be capable of discovering and localizing ectopically erupted and impacted teeth, by auto-inspection of panoramic x-rays for creating a report for patient treatment and consultation.

Further, the present DCVA system and method may utilize unique artificial intelligence systems called a "Smart Composer" and "Smart Decomposer" which may be capable of auto-decomposing standard Orthodontics composite clinical images into constituent component images for creating a report for patient treatment and consultation. The Smart Composer and Smart Decomposer systems may also be capable of reversing the operation, by correctly selecting the proper clinical images and creating a standard Orthodontics composite clinical image for creating a report for patient treatment and consultation.

Still further, the present DCVA system and method may utilize a unique artificial intelligence system called a "Smart Anonymizer" which may be capable of anonymizing patient's data, by removing all textual and facial identifications from visual assets for creating a report for patient treatment and consultation.

The prior art in the field fails to describe a DCVA system and method which is easy to use and efficient as in the present application.

BACKGROUND

Starting the mid nighties of the last century, a huge amount of dento-craniofacial visual assets (herein referred as 'DCVA') have been continuously accumulating within many different repositories, ranging from universities, government agencies, insurance companies, research facilities, publishers, down to as small as polyclinics. Major World Wide Web search engines, like Google®, have also given access to a large amount of DCVA through their web search engines.

One major problem facing the owners and users of these DCVA repositories is the complete absence of a system capable of parsing the many repositories, automatically recognizing the content, automatically building labels and metadata, and then optionally saving metadata in a query-ready computer formats to be used to respond to intelligent interrogations from all types of users. Another major problem is that all web search engines, like Google®, once applied to highly specialized data like DCVA fail badly by returning completely irrelevant images to the searched phrases.

Proper DCVA search results are required for many aspects of dentistry, including providing information to insurance companies for pre-approval of expensive dental procedures. Dental Insurance treatment authorization for orthodontics cases are generally based on human inspection and evaluation of each DCVA individual case. This human dependent process is subjective and a very slow and costly procedure, prone to human error and bias.

Anonymization of patients DCVA in order to conform to privacy standards and legislations, for the large amount of digital assets, is a very slow and costly procedure, but is generally required for research, analytics, business intelligence, machine learning and others. Decomposing composite DCVA into labeled individual visual assets, as part of data preparation for any required procedure is also a very slow and costly procedure. Further, selecting the proper individual visual assets and composing them in a new composite image (visual asset), conforming to standards, is a very slow procedure.

The multiple artificial intelligence systems and methods in the present system and method are aimed to solve all the forgoing problems.

SUMMARY OF THE INVENTION

This present system and method provide artificial intelligence systems and methods for automatic identification, localization, recognition, understanding, labelling, analyzing, assessing, deciding and planning related to dentocraniofacial visual assets ('DCVA') for creating a report deriving an outcome for patient treatment and consultation. The reports may be physical reports in one embodiment.

In one embodiment, the Dental Classifier portion of the present system and method includes the steps of automatically: (1) typing DCVA such as, for example, as x-rays and clinical images of a patient, into a computer; (2) categorizing each discovered type of asset, relative to its nature (I.E.: intra-oral, extra-oral, etc.); (3) classifying items pertaining to each type and category (I.E.: bitewing, panoramic, etc.); (4) auto-correcting the orientation of the relevant asset according to standards; (5) recognizing anatomical modifiers (I.E.: upper, lower, right, left.) of the patient; (6) auto-generating of accurate metadata relative to each asset; and finally (7) saving metadata to different types of query-ready formats for creating a report for patient treatment and consultation.

In another embodiment of the present system and method, the Search Engine Filter Booster portion of the present system and method includes the steps of: (1) integrating and boosting generic web search engines; (2) automatically filtering results returned from generic search engines, like the Google® search engine, and presenting only the proper results to the end user; and (3) installing the results of the search locally to accurately query any existing DCVA repositories for creating a report for patient treatment and consultation.

In another embodiment of the present system and method, the Smart Decomposer portion of the present system and method may include the steps of: (1) recognizing composite images of a patient; (2) discovering the constituent images presented in the composite image; (3) extracting (decomposing) each individual image from the composite image; and (4) saving each extracted images in its proper folder, using the proper identification for creating a report for patient treatment and consultation.

In another embodiment of the present system and method, the Smart Composer portion of the present system and method may include the steps of: (1) locating the proper image views within any computer folders; (2) creating a new composite image containing the proper views according to the required type of composite image; and (3) saving the newly created composite image in its proper folder, using the proper identification for creating a report for patient treatment and consultation.

In another embodiment of the present system and method, the Smart Anonymizer portion of the present system and method may include the steps of: (1) recognize textual and facial identifiers in DCVA; (2) discarding the recognized identifiers; (3) creating a new asset, free from any textual or facial identifier; and (4) saving the newly created anonymized asset in its proper folder, using the proper identification for creating a report for patient treatment and consultation.

In another embodiment of the present system and method, the Dental Insurance Treatment Auto-Authorizer portion of the present system and method may include the steps of: (1) accepting patient lateral cephalometric x-ray; (2) accepting patient panoramic x-ray; (3) accepting patient composite image including five or eight clinical views; (4) feeding each type of presented patient assets to the proper present system and method AI Engine (I.E.-(i) Landmarks localizer, (ii) Ectopic Eruption Discoverer (iii) Dental Arch Inspector); (5) analyzing the proper asset and produce the proper sections of the HLD Score Sheet; (6) consolidating all results in a single detailed report; (7) generating a summary report listing "Accepted" and "Rejected cases; (8) providing the information via downloadable or non-downloadable versions; and (9) saving the consolidate report in its proper folder, using the proper identification for creating a report for patient treatment and consultation.

In another embodiment of the present system and method, the Landmarks Localizer portion of the present system and method may include the steps of: (1) recognizing and differentiating between right Lateral Cephalometric x-rays (standard view) and left view; (2) correcting the left view, by mirroring it, to the standard right view; (3) discovering and localizing major cephalometric landmarks related to dental insurance; (4) marking (drawing) each localized landmark; (5) performing the proper quantitative analysis on the localized points; (6) generating the HLD score report relative to the findings; (7) consolidating the results with the output results of other system and method engines to produce the final "Acceptance/Rejection" report; and (8) saving the generated report in its proper folder, using the proper identification, along with the marked x-rays for creating a report for patient treatment and consultation.

In another embodiment of the present system and method, the Ectopic Eruption Discoverer portion of the present system and method may include the steps of: (1) recognizing panoramic x-rays; (2) analyzing the panoramic x-ray and localizing (i) Ectopic Eruptions (ii) Impactions (iii) Mixed Dentition; (3) marking (drawing) the area for each localized occurrence; (4) labelling each panoramic x-ray with the proper metadata; and (5) saving the generated report in its proper folder, using the proper identification, along with the marked x-rays for creating a report for patient treatment and consultation.

In one embodiment, the present system and method does not rely on dental arch inspector analysis.

For a more complete understanding of the above listed features and advantages of the present system and method, reference should be made to the detailed description and the drawings.

BRIEF DESCRIPTION OF THE DRAWINGS

FIGS. 7, 8 and 9, illustrate a detailed listing of all layers of the neural network designed, implemented and used in one embodiment of the present system and method for the DCVA Classifier, Booster Filter, Decomposer, Composer, and Anonymizer.

For a general understanding of the environment for the systems and methods disclosed herein as well as the details for the systems and methods, reference is made to the drawings. In the drawings, like reference numerals have been used throughout to designate like elements.

DETAILED DESCRIPTION

Figure 1:
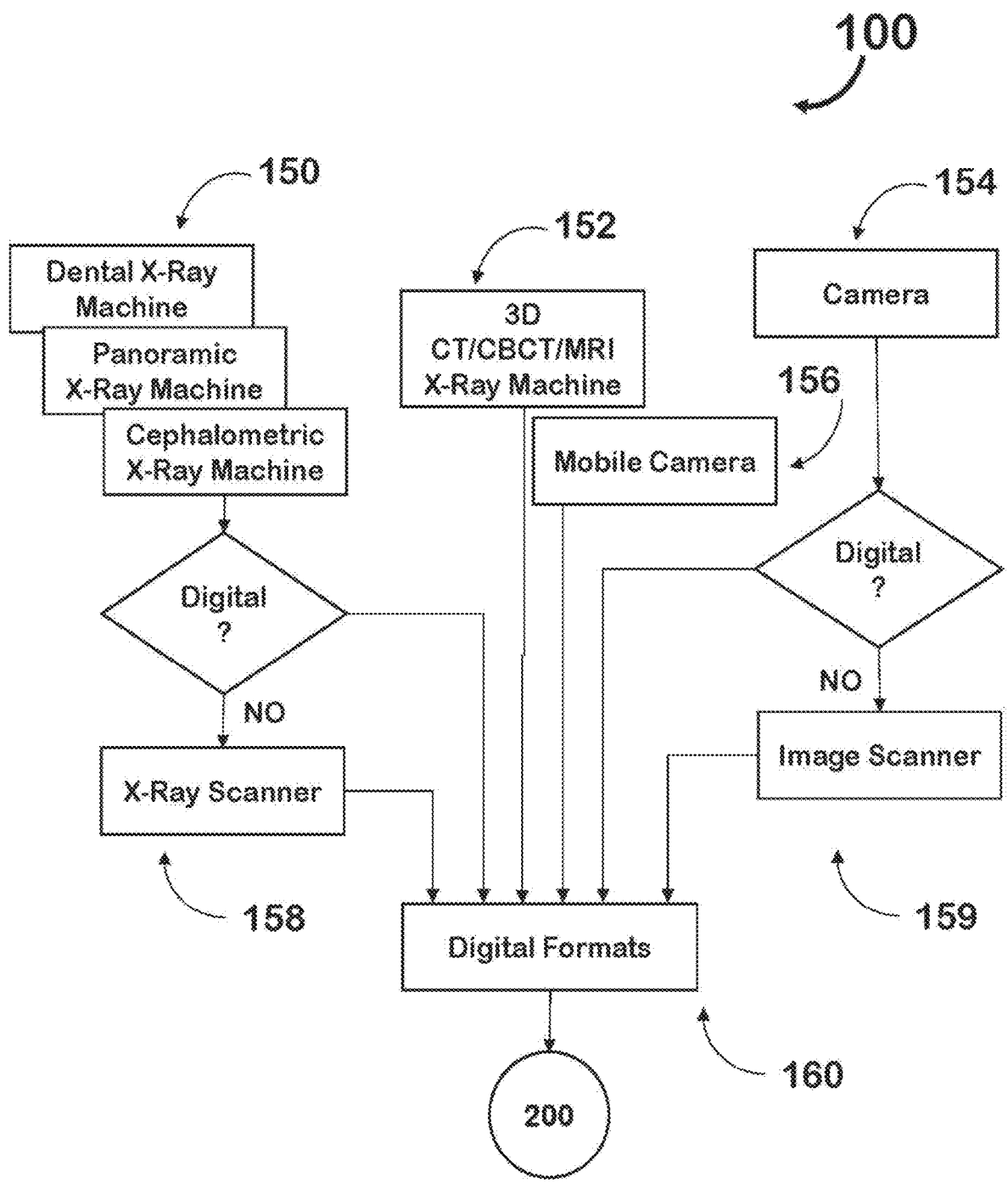
FIG. 1 illustrates a schematic diagram depicting how the datasets (DCVA) are acquired, and digitized into machine-readable format, if required.
Figure 2:
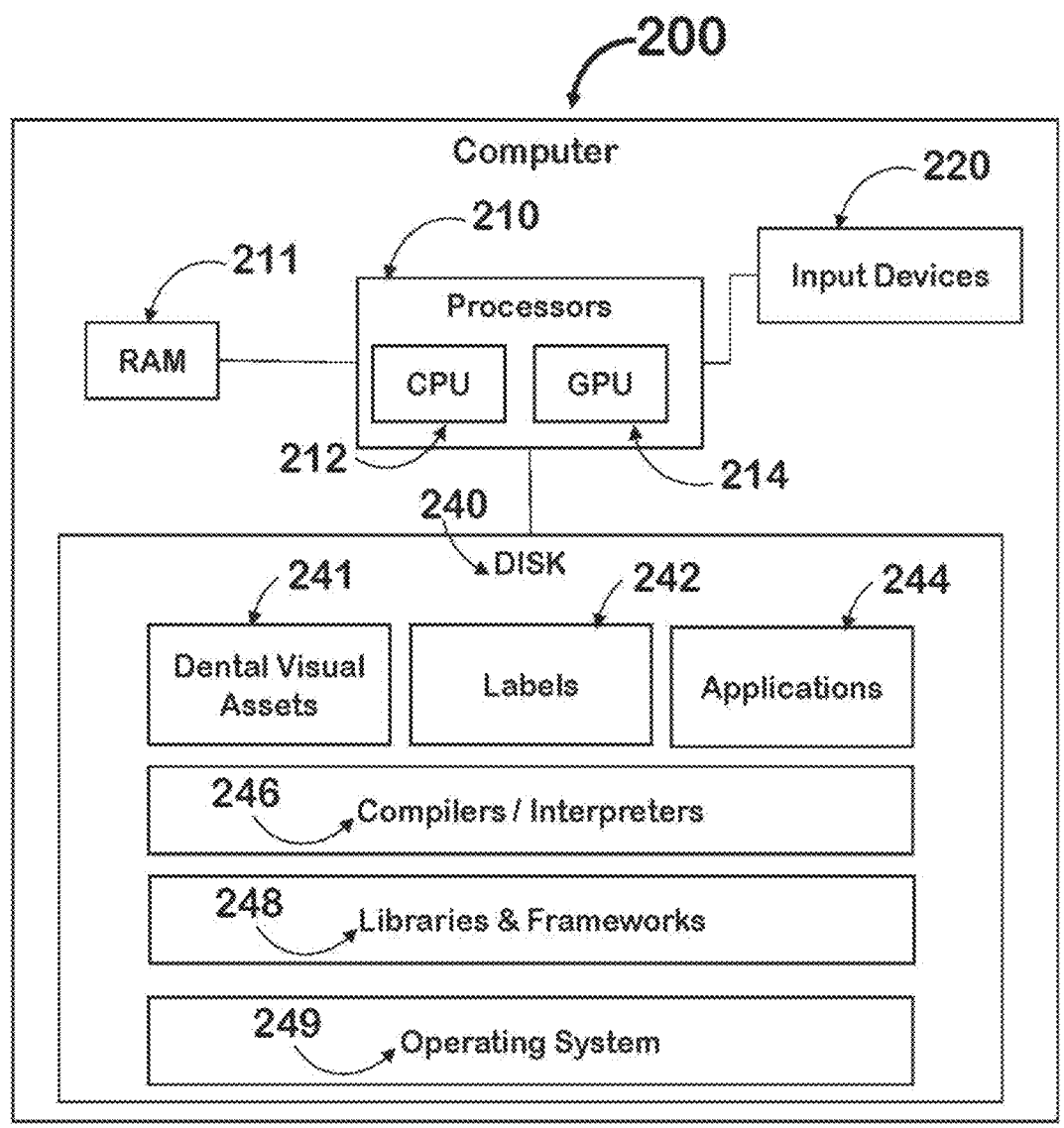
FIG. 2 illustrates a schematic diagram of the computer system infrastructure, including all relevant layers.

The present system and method provide artificial intelligence systems and methods for automatic identification, localization, recognition, understanding, labelling, analyzing, assessing, deciding, planning related to dento-craniofacial visual assets ('DCVA').

As used herein, the term "object" refers to any physical item that may be suitable for scanning and imaging with, for example, an x-ray scanner. In a medical context, examples of objects may include, but are not limited to, portions of the body of a human or animal, or models that correspond to the body of the human or animal. For example, in dentistry objects include the interior of a mouth of the patient, a negative dental impression formed in compliance with the interior of the mouth, and a dental image of the teeth in occlusion. As used herein, the term "element" refers to a portion of the object, and an object comprises one or more elements. In an object, at least one element is referred to as a "static" or "reference" element that remains in a fixed location relative to other elements in the object. Another type of element is a "dynamic" element that may move over time in relation to other elements in the object. In the context of a mouth or dental casting of a mouth, the palate (roof of the mouth) is an example of a static element, and the teeth are examples of dynamic elements.

Referring now to the drawings, the present system and method 100 is illustrated as a schematic diagram depicting how the dento-craniofacial visual assets (DCVA) are generated. The DCVA are generally either x-rays or images (such as photographs). X-rays 150 are generally generated from a dental x-ray machine, a panoramic x-ray machine, a cephalometric x-ray machine CT, CBCT and/or an MRI machine 152. Old modalities generally produced only printed films, which would then have to be digitized using an x-ray scanner (x-ray digitizer) 158 and stored in proper file formats 160. Images, collected from cameras 154, mobile cameras 156 or other sources, may also be digitized 159 to acceptable format 160, if they are not already in machine-readable formats.

In an embodiment, the present method and system utilizes a computer 200. The computer 200 may include processors 210, random access memory (RAM) 211, a non-volatile data storage device (disk) 240, an output display device, and one or more input devices 220. The processor 210 may include a central processing unit (CPU) 212 and multiple graphical processing units (GPU) 214. The CPU 212 may be a fast processor from, for example, the Intel x86 family, with 12 virtual cores. Two GPUs 214 may include digital processing hardware that is configured for floating point number crunching, in a massively parallel configuration. Each GPU 224, NVIDIA VOLTA may include 5120 CUDA cores, 640 Tensor cores and 12 GB HBM2 RAM, for a total of, for example, 10240 CUDA cores, 1280 Tensor cores and 24 GB HBM2 RAM. In another embodiment, the CPU 212 and the two GPUs 214 may be discrete components that communicate using an input-output (I/O) interface, PCI express data bus.

The processor 210 may be operatively connected to the storage disk 240 to store and retrieve digital data from the storage disk 240 during operation of the present system and method. The storage disk 240 may be a solid-state data storage device, backed by magnetic disks suitable devices that stores digital data for storage and retrieval by the processor 210. The storage disk 240 may be a non-volatile data storage device that retains stored data in the absence of electrical power. While the storage disk 240 is depicted in the computer 210, some or all of the data stored in the storage disk 240 may be optionally stored in one or more external data storage devices that are operatively connected to the computer 200 by, for example, multiple universal serial bus units (USB) and/or through local area network (LAN). The present software applications 244 operate in conjunction with an underlying operating system (OS) 249 and software libraries 248. The storage disk 240 may also store digitized data (dento-craniofacial visual assets) 241 and/or labels 242 that the computer 200 receives from different sources 100.

In addition to datasets and associated labels and metadata, the storage disk 240 may store programing languages 246 used in aspect of the current system and method, mainly C++ compiler and Python 3.5 interpreters. The storage disk 240 may additionally store the frameworks 248 used to build the neural networks of the current system and method, mainly TensorFlow 1.10. The frameworks may be built over different libraries 248, mainly CUDA, CUDNN and other NVIDIA GPU based libraries. All these libraries may be also stored on the storage disk 240.

The present RAM 211 of the system of method may include one or more volatile data storage devices having dynamic RAM devices. The processor 210 may be operatively connected to the RAM 211 to, for example, enable storage and retrieval of digital data. In one embodiment, the CPU 212 and the GPU 214 are each connected to separate RAM devices. During operation, the processor 210 and data processing devices in the computer 200 store and retrieve data from the RAM 211. As used herein, both the RAM 211 and the storage disk 240 are referred to as a "memory" and program data, scanned sensor data, graphics data, and any other data processed in the computer 200 are stored in either or both of the storage disk 240 and RAM 211 during operation.

The display device is operatively connected to the one of the GPU 214 in the processor 210 and is configured to display textual and graphics objects and elements in the objects.

Figure 3:
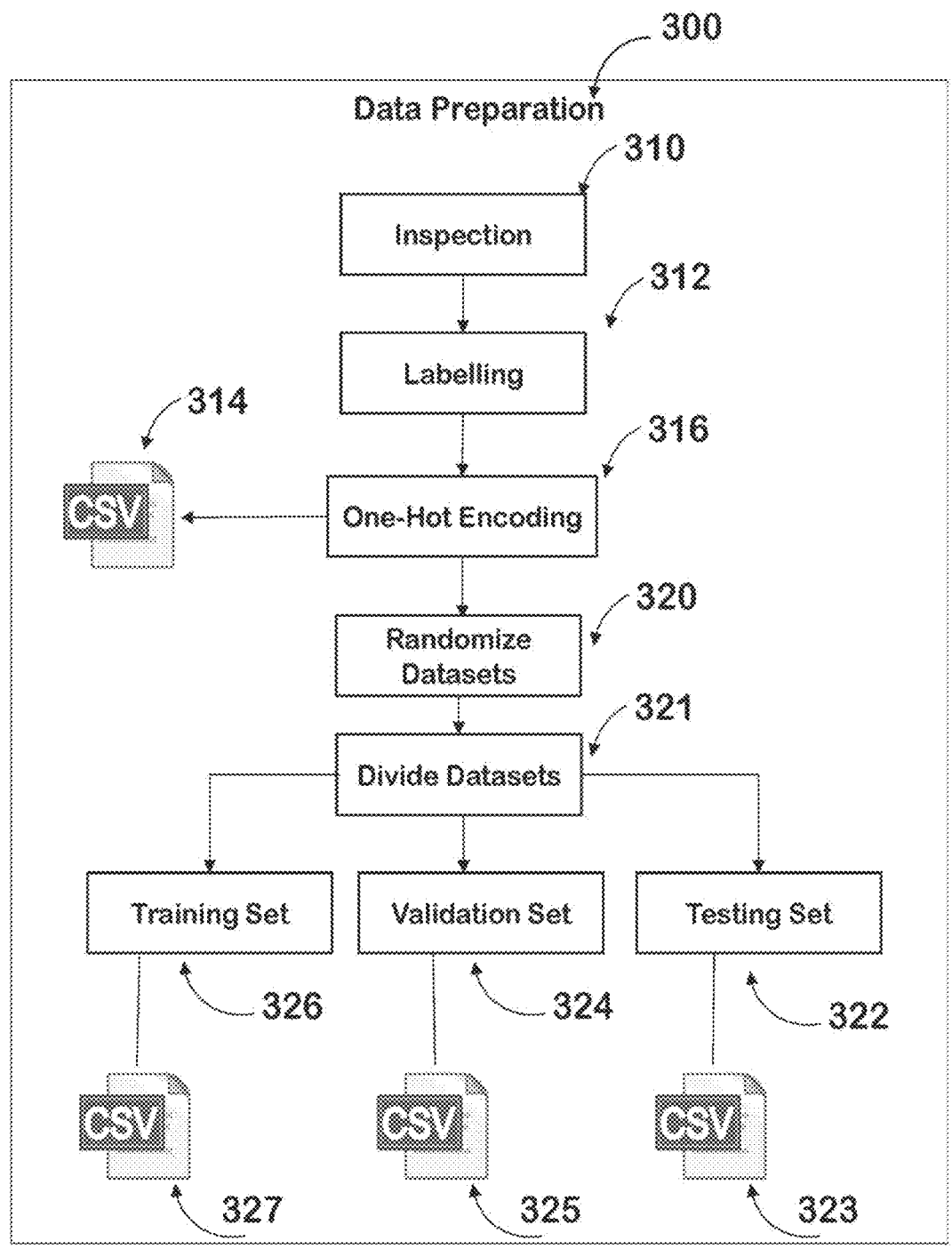
FIG. 3 illustrates a block diagram summarizing the process of data preparation, labelling, one-hot-encoding, randomizing and dividing of the datasets into three functional groups of the present system and method.

The process 300, depicted in FIG. 3, outlines the different tasks required in order to generate the proper datasets for training, validation and testing. Once the anonymized data are collected from different sources, according to privacy legislations, they are stored on the storage disk 240 and may be backed up on other external devices as described above.

As illustrated in FIG. 3, the first task/step in the present system and method is the preparation of data 300 by data inspection 310. Each DCVA may be inspected to insure it is conforming to the standards required by the present system and method, and insures it belongs to one of the targeted classes. The data may then be labeled 312, using the English (or alternative) terms identifiers from FIG. 4. The English terms identifiers are then translated to one-hot-encoding 316 and saved to storage disk 240 in comma separated values (CSV) format 314. The stored file contains each asset full name and disk path, its dimensions, number of color channels, its English term identifier and its one-hot-encoded array.

For process 1306 and 1308 the proper DCVA were manually labelled by boxing all anatomical and developmental areas relative to the process in the present system and method. All box information were saved in XML computer file formats.

In one embodiment, one-hot-encoding 316 is performed. One-hot-encoding 316 a process by which categorical identifiers (variables) are converted into a form that could be provided to Deep Learning algorithms in a mathematical form to do a better job in the training and prediction. One-hot-encoding translates each identifier into a group of bits among which the legal combinations of values are only those with a single high (1) bit and all the others low (0).

The full-inspected datasets may then be randomized 320 and distributed into, for example, three datasets 321. The training 326 dataset may be 85% of the total assets, while the validation 324 dataset may be 10% and the testing 322 dataset may be 5% of the total assets. CSV files 327, 325, 323 are generated for each group dataset and saved to the storage disk 240.

Figure 4:
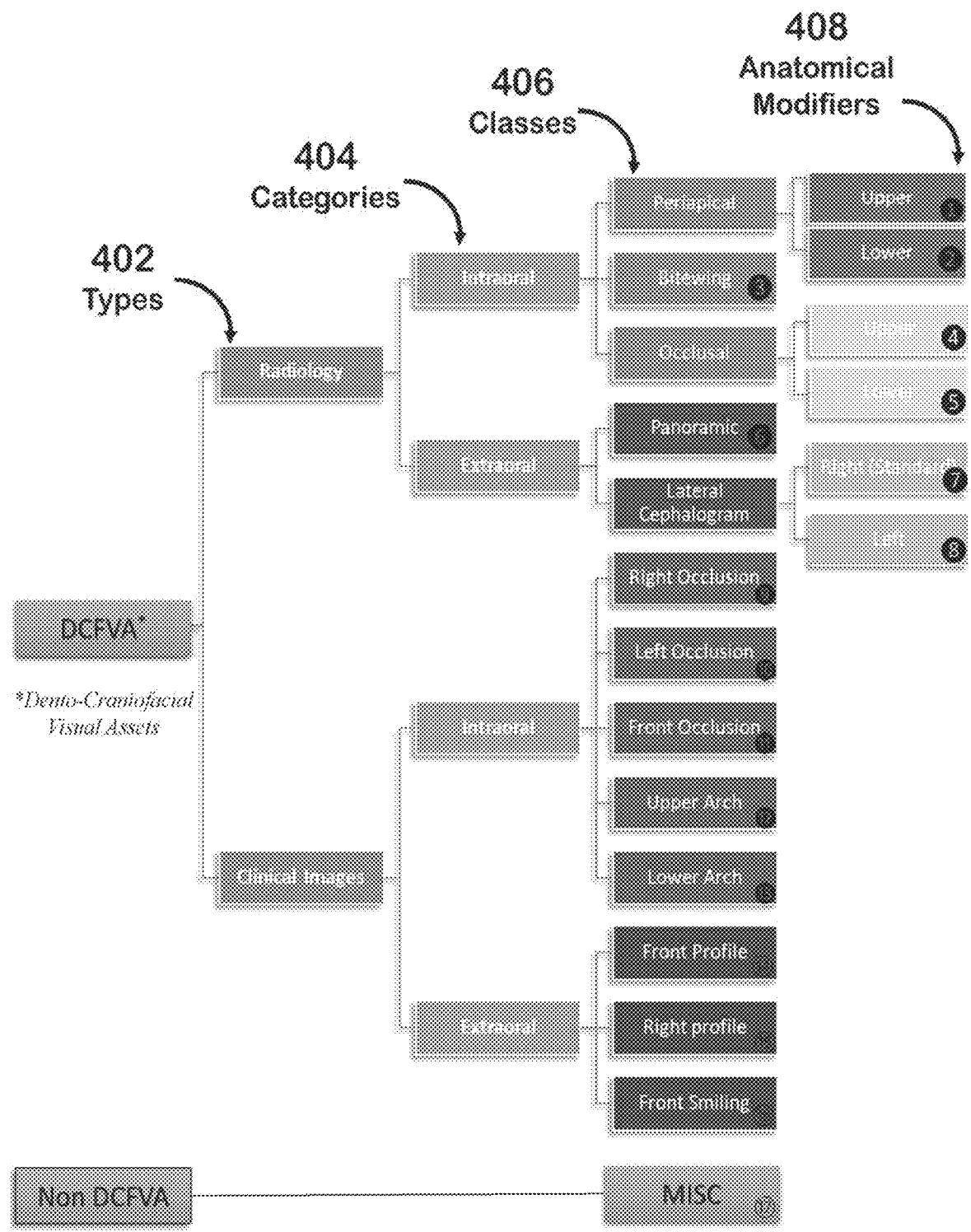
FIG. 4 illustrates a schematic representing the hierarchy of DCVA classes, categories and types, including anatomical modifiers of the present system and method. Seventeen classes are depicted and are used to label the datasets, and translate the final inferenced results into English dental terms equivalent to the internal one-hot-encoded identifiers.

Referring now to FIG. 4, in an embodiment, a schematic representing the hierarchy of DCVA classes, categories and types, including anatomical modifiers is provided. Sixteen classes are depicted and are used to label the datasets, and translate the final inference results into English dental terms equivalent to the internal one-hot-encoded identifiers.

Figure 5:
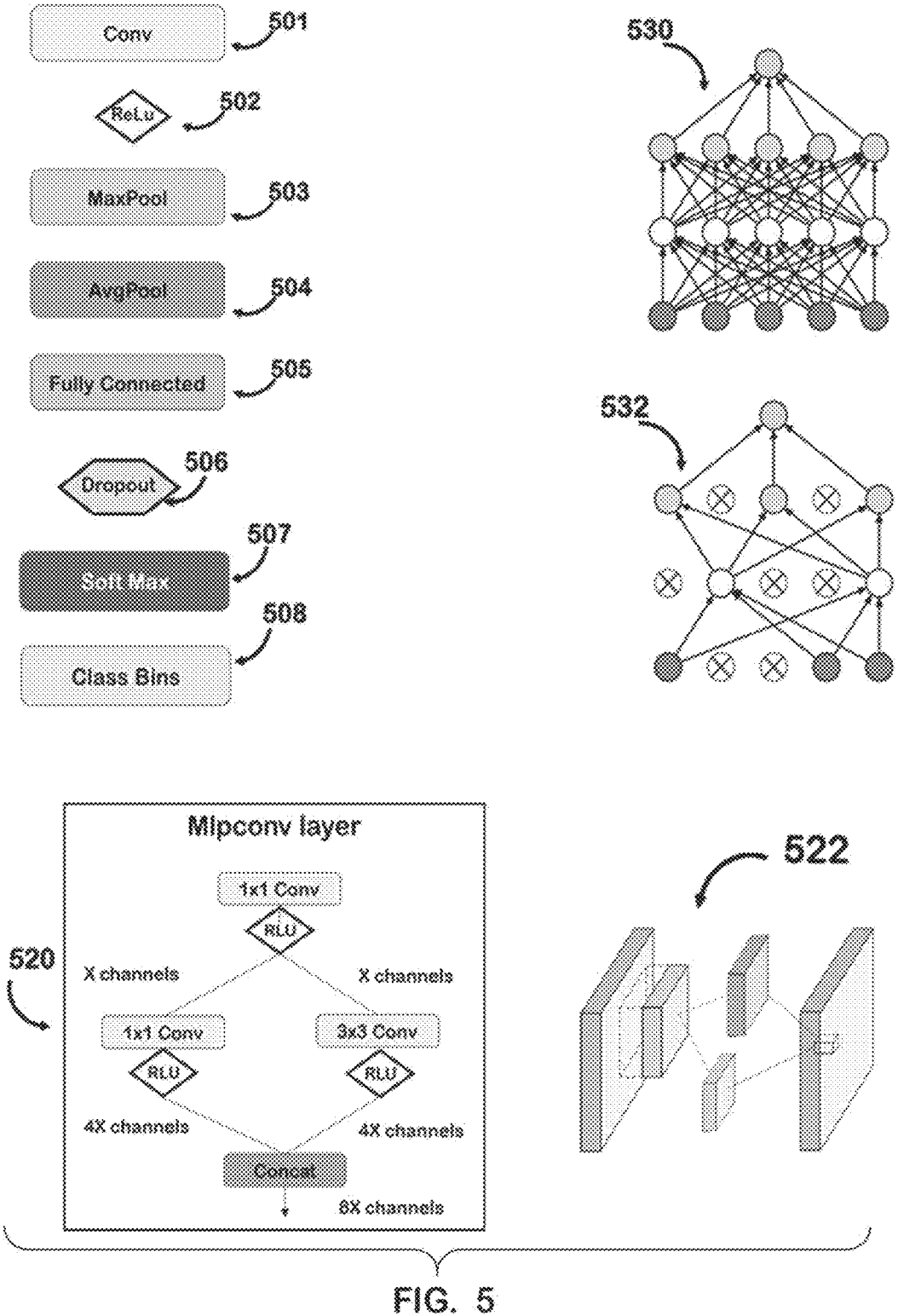
FIG. 5 illustrates schematics representing the technical building blocks of the neural network designed and technical concepts, implemented and used in one embodiment of the present system and method.

Referring now to FIG. 5, in an embodiment, a schematic representation of all the technical building blocks of the neural network designed, implemented and used in the aspect of the current system and method is provided.

Block 501 represents the building block of convolutional neural networks (CNN) designed and implemented in an embodiment of the present system and method. In mathematics convolution is a mathematical operation on two functions to produce a third function that expresses how the shape of one is modified by the other. The term convolution refers to both the result function and to the process of computing it. Convolutional networks were inspired by biological processes [1] in that the connectivity pattern between neurons resembles the organization of the animal visual cortex. Individual cortical neurons respond to stimuli only in a restricted region of the visual field known as the receptive field. The receptive fields of different neurons partially overlap such that they cover the entire visual field. A CNN consists of an input and an output layer, as well as multiple hidden layers. The hidden layers of a CNN typically consist of convolutional layers, RELU 502, 604 layer (activation function), pooling layers 608, fully connected layers and normalization layers.

The rectified linear unit ReLu 502 is an activation function defined as the positive part of its argument $f(x)=\max(0, x)$, where x is the input to a neuron. The graph 604 shows plots the behavior of the ReLu function. Pooling 504, 505, combine the outputs of neuron clusters at one layer into a single neuron in the next layer [2]. For example 608, max pooling uses the maximum value from each of a cluster of neurons at the prior layer, while average pooling, which uses the average value from each of a cluster of neurons at the prior layer.

Fully connected layers 505 connect every neuron in one layer to every neuron in another layer. It is in principle the same as the traditional multi-layer perceptron neural network (MLP). Dropout 506 refers to dropping out units (both hidden and visible) in a neural network. Dropout is a regularization technique for reducing overfitting in neural networks by preventing complex co-adaptations on training data. An example showing the original network 530 before dropout, and the network 532 after dropout is shown in FIG. 5.

Cross-entropy loss 602, measures the performance of a classification model whose output is a probability value between 0 and 1. Cross-entropy loss increases as the predicted probability diverges from the actual label. So predicting a probability of 0.012 when the actual observation label is 1 would be bad and result in a high loss value. A perfect model would have a log loss of 0.

Figure 6:
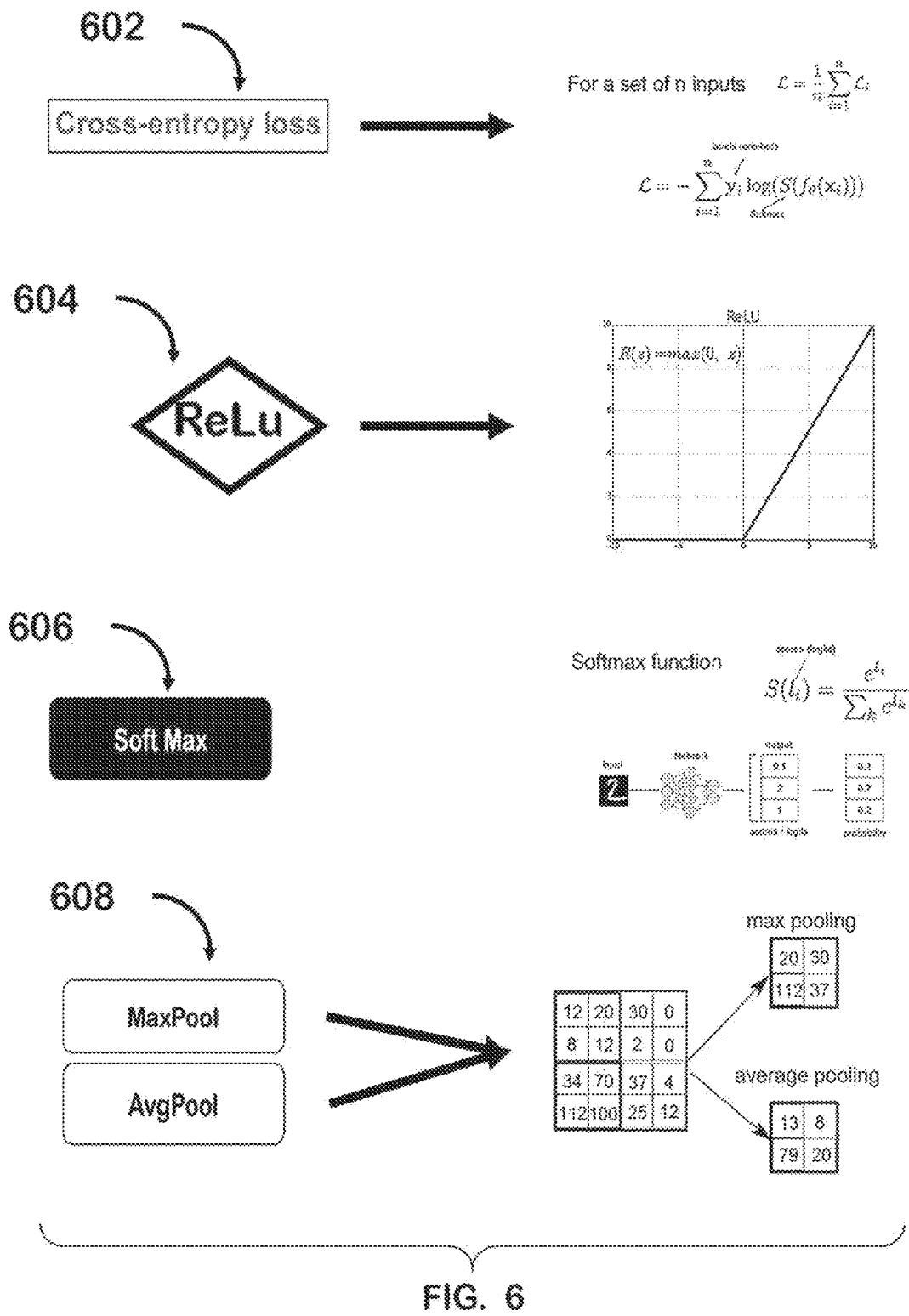
FIG. 6 illustrates a continuation of FIG. 5, showing additional technical concepts used and their explanation in one embodiment of the present system and method.

The SoftMax function 507 takes an un-normalized vector, and normalizes it into a probability distribution. That is, prior to applying SoftMax, some vector elements could be zero, or greater than one; and might not sum to one; but after applying SoftMax, each element becomes in the interval [0, 1]. An illustration of the SoftMax function 606 is shown in FIG. 6.

Class bins 508 are the last nodes in the network, they are exactly equal to the number of classes the network is able to predict. After prediction, each bin will contain the probability of that class under test.

In order to achieve the required quality, robustness and accuracy, our designed and implemented network in the aspect of the current system and method, is conceived as a deep network of more than 40 layers deep. Standard implementation of convolutional neural networks of such depth will result in approximately 60 million trainable parameters, increasing the computational and time requirements for training to a prohibiting level. As a solution, the present system and method implemented a compression repeating-block 520, 522, inspired by a network in Network Model [4] and the SqueezeNet Model [5]. This design resulted in a reduction of the total number of trainable parameters from 60 million approximately down to 729,165 trainable parameters. The total memory requirements and training time fell within the capabilities of the computer 200, processor 210, and the two NVIDIA Volta GPUs 214.

FIGS. 7, 8, and 9 are a full listing of the architectural model of the full neural network designed and implemented in the respect of the present system and method. Layer names are printed, as well as their types and operations. The input layer expects square images of 227 pixel per side, and channel depth of three. The present system and method use, for example, three color channels to insure that the system and method can deal with color and gray scale images equally easy. After a preliminary convolution and pooling layers, subsequent layers are mostly composed by a repeating structure 512, 522, FIG. 5, inspired by the Network In Network model [4] and the SqueezeNet model [5]. Each repeating structure starts with an X number of channels of 1×1 filters convolutions, followed by two parallel convolutions, the first is 4× channels 1×1 filters, the second is 4× channels 3×3 filters. This is followed by the concatenation of results of both parallel convolutions in an 8× channels structure. The variable X range from 16 to 128, resulting in the following structure composition depth, starting at 16, 64, 128, and ending at 64, 256, 512 depth channels. Rectified linear units (ReLu) 502, 604, is used throughout all relevant layers. Two pooling functions were implemented, maximum pooling (MaxPooling), implemented all over the network, except for the layer before the last, where we used average pooling (AvgPooling). Average pooling is more meaningful and interpretable as it enforces correspondence between feature maps and categories, which is made possible by a stronger local modeling [4]. Dropout 506 was used only at the full depth of the network. Soft max 507, 606 is applied at the last layer, feeding the final class bins 508.

The neural network in FIGS. 7, 8, and 9 designed and implemented in the respect of the present system and method was trained using a dataset composed in the average about 3,000 x-ray/image for each type/category/class, including the same number of miscellaneous images from the Common Objects in Context collection [6], for a total of about 40,000 image. Original images have a width within the range of 1000-2000 pixel and height within 1000-2000 pixels. All images were converted to three channel, JPG formats.

The neural network in FIGS. 7, 8, and 9 designed and implemented in the respect of the present system and method was trained for 500 epochs. The present system and method use the Root Mean Square Propagation (RMSprop) optimizer in order to adapt the learning rate each of the parameters. Our start-learning rate is 0.0001. Weight are initialized using the glorot uniform initializer, which draws samples from a uniform distribution within [-limit, limit] where limit is SquareRoot(6/M+L)) where M is the number of input units in the weight tensor and L is the number of output units in the weight tensor. At the end of training process, the neural network designed and implemented in the respect of the present system and method achieved an almost perfect accuracy score, loss 0.0120, categorical accuracy 0.9961, top k categorical accuracy 1.0000, validation loss 0.1282, validation categorical accuracy 0.9749, and validation top k categorical accuracy 0.9985.

The trained neural network in FIGS. 7, 8, and 9, designed and implemented in the respect of the present system and method, is saved Saves to a Hierarchical Data Format version 5 (HDF5) file on disk 240. The saved model contains the model's configuration (topology), the model's weights, and optimizer's state. The saved model can be re-instantiated in the exact same state, without any of the code used for model definition or training. This file is used to seed all subsequent predictions.

Figure 11:
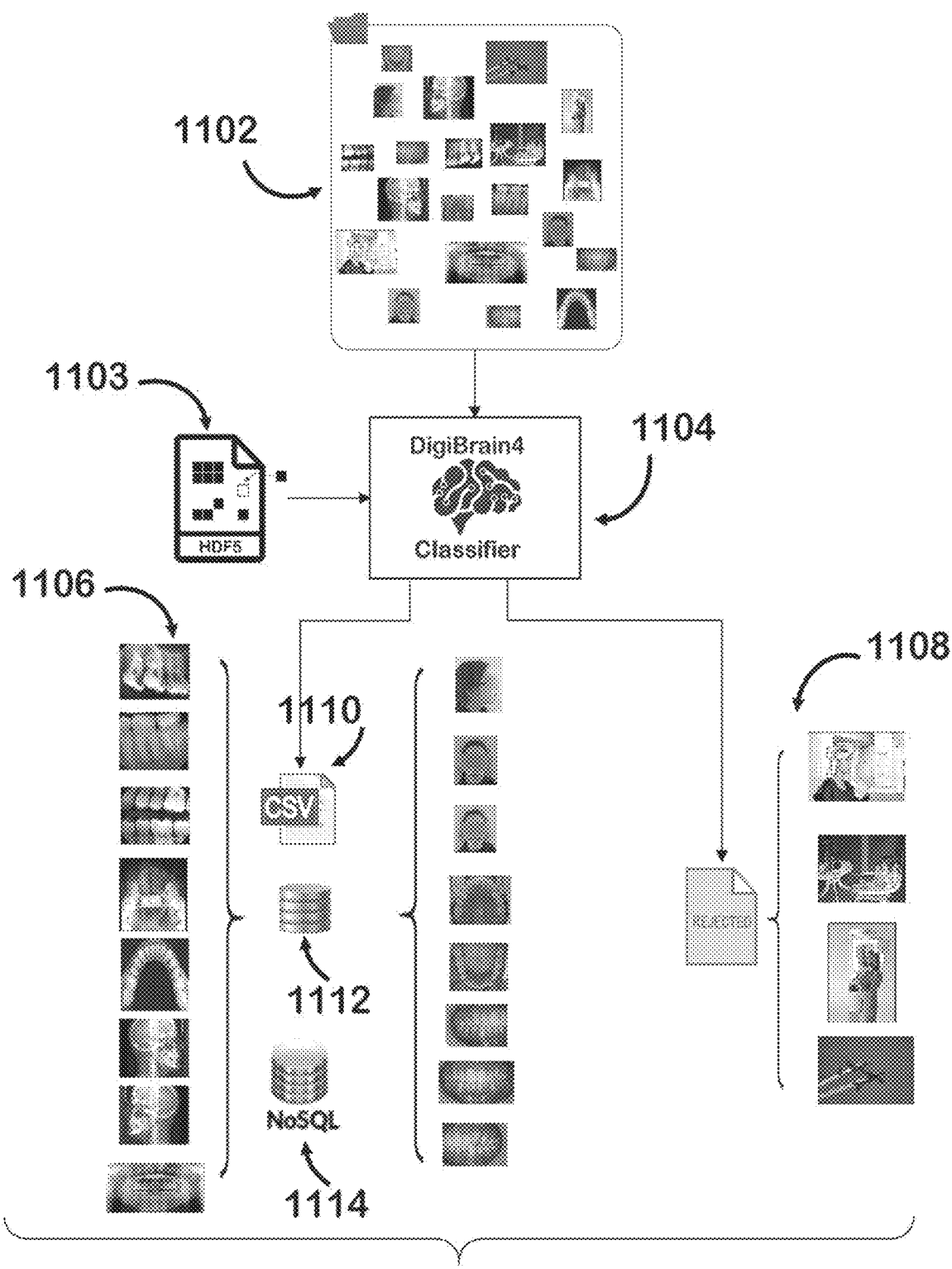
FIG. 11 illustrates one embodiment of a block diagram describing the DCVA classifier mode of action, including input and output data of the present system and method.

Block diagram shown in FIG. 11, summarize the process of predicting the correct type/category/class of DCVA, which can range from a single asset up to any number of assets 1102 that can be stored and fed from disk storage. The neural network in FIGS. 7, 8, and 9, designed, implemented and trained in the respect of the present system and method, is retrieved from the HDF5 file 1103 saved after the end of training, and containing the model's configuration (topology), the model's weights, and optimizer's state. Once the file may then be loaded into memory 211 (RAM) it represents a re-instantiation of the trained model in the exact same state, ready for prediction. Average prediction time is less than 0.02 sec.

In one embodiment, the re-instantiated classifier 1104, in respect of the present system and method, will predict the correct type/category/class for each asset, and automatically generates the corresponding metadata, to be save in many formats, mainly CSV files 1110, Relational Database 1112 or NoSQL Database 1114. In one embodiment, the re-instantiated classifier 1104, in respect of the present system and method, will recognize and reject all non-relevant assets 1108. In another embodiment, classifier 1104 may be used to search for a specific DCVA class from with any repositories, returning only the assets pertaining to the searched-for class.

Figure 12:
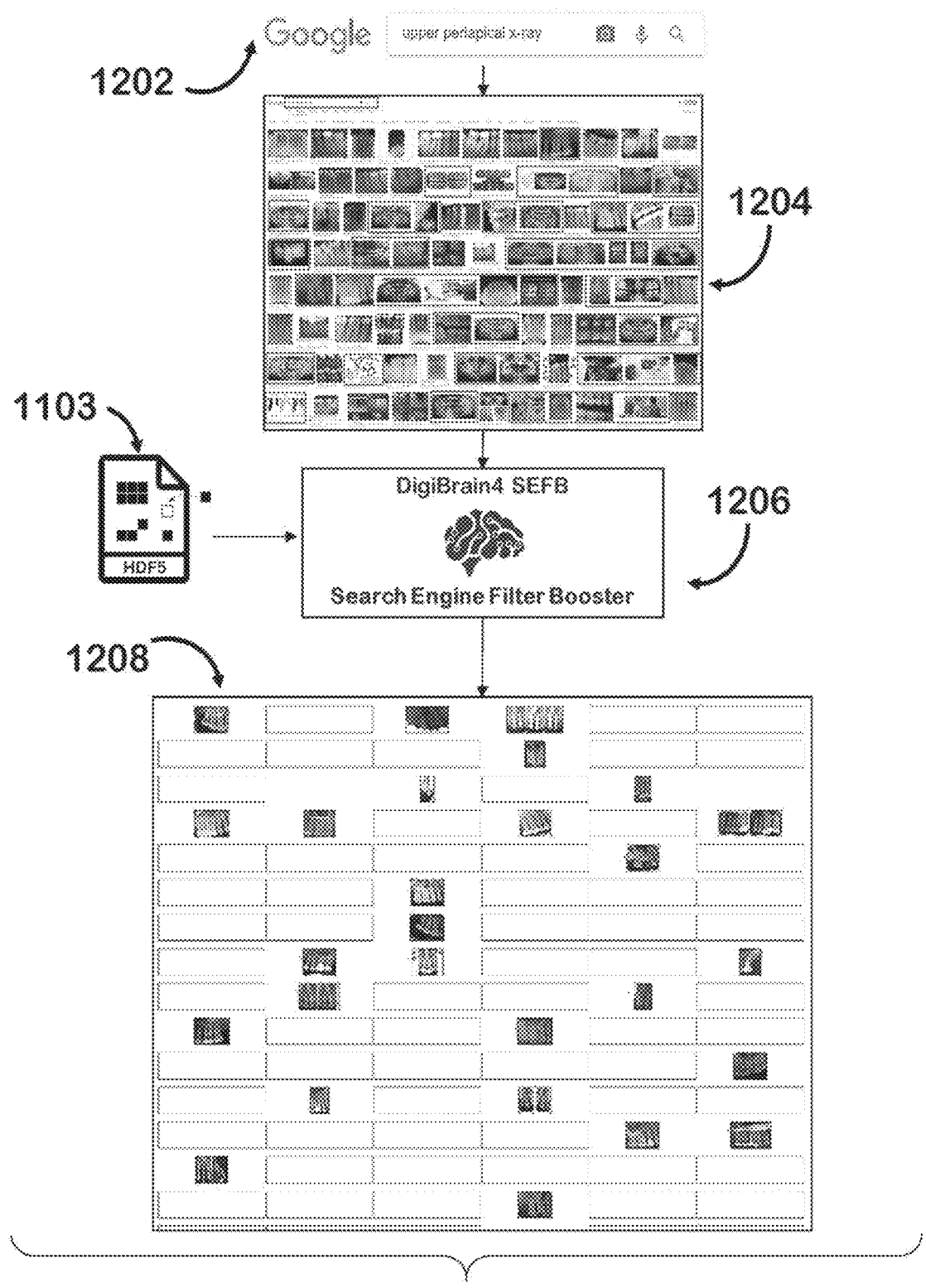
FIG. 12 illustrates one embodiment of a block diagram describing the Google search-engine filter-booster, including input and output.

In respect of the present system and method, the present search-engine filter-booster shown in FIG. 12 may be a plugin capable of filtering the results returned from generic search engines. The filtration process will return only the assets pertaining to the searched-for terms. The search engine will submit the search phrase (terms) to Google search engine 1202 transparently in the background, then collect the results by Google search engine. The returned results 1204 will be automatically submitted to search-engine filter-booster, in respect of the present system and method 1206, which is re-instantiated from the training HDF5 file 1103. The booster will filter Google results and only returns the searched-for assets as per the search phrase (terms) 1208.

Figure 10:
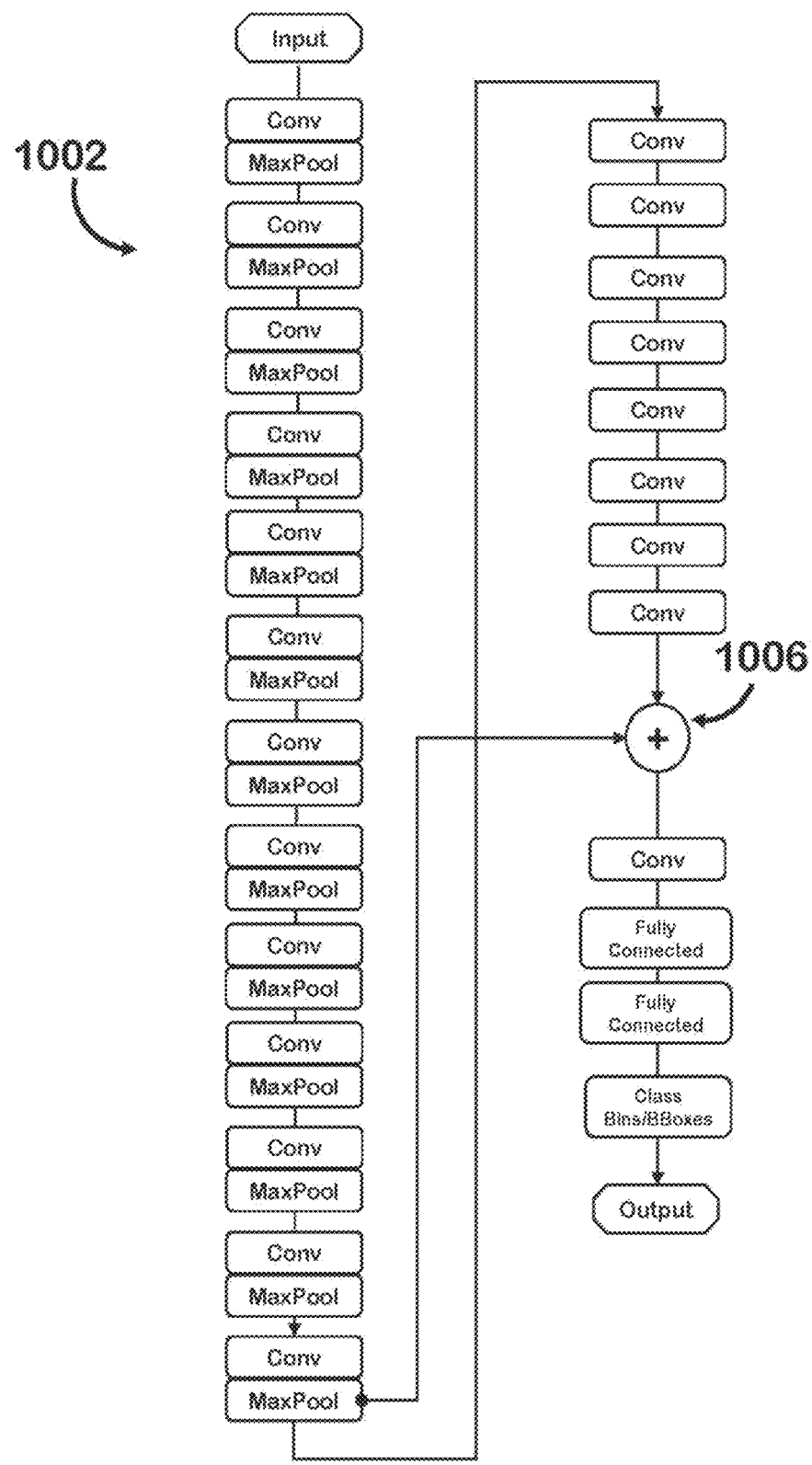
FIG. 10 illustrates a detailed diagram of the neural network designed, implemented and used in one embodiment of the present system and method for the DCVA Localizer and Ectopic Discoverer.

In respect of the present system and method, the neural network diagram depicted in FIG. 10, represent the deep network used in the landmark localization and ectopic eruption discoverer.

The neural network architecture 1002 is inspired by the object detection and localization network described in [7] with slight modifications. An important feature is the use of the residual information collected and abstracted at the depth of the convolutional layers and injected directly into the dense layers at the bottom 1006 of the network.

Figure 13:
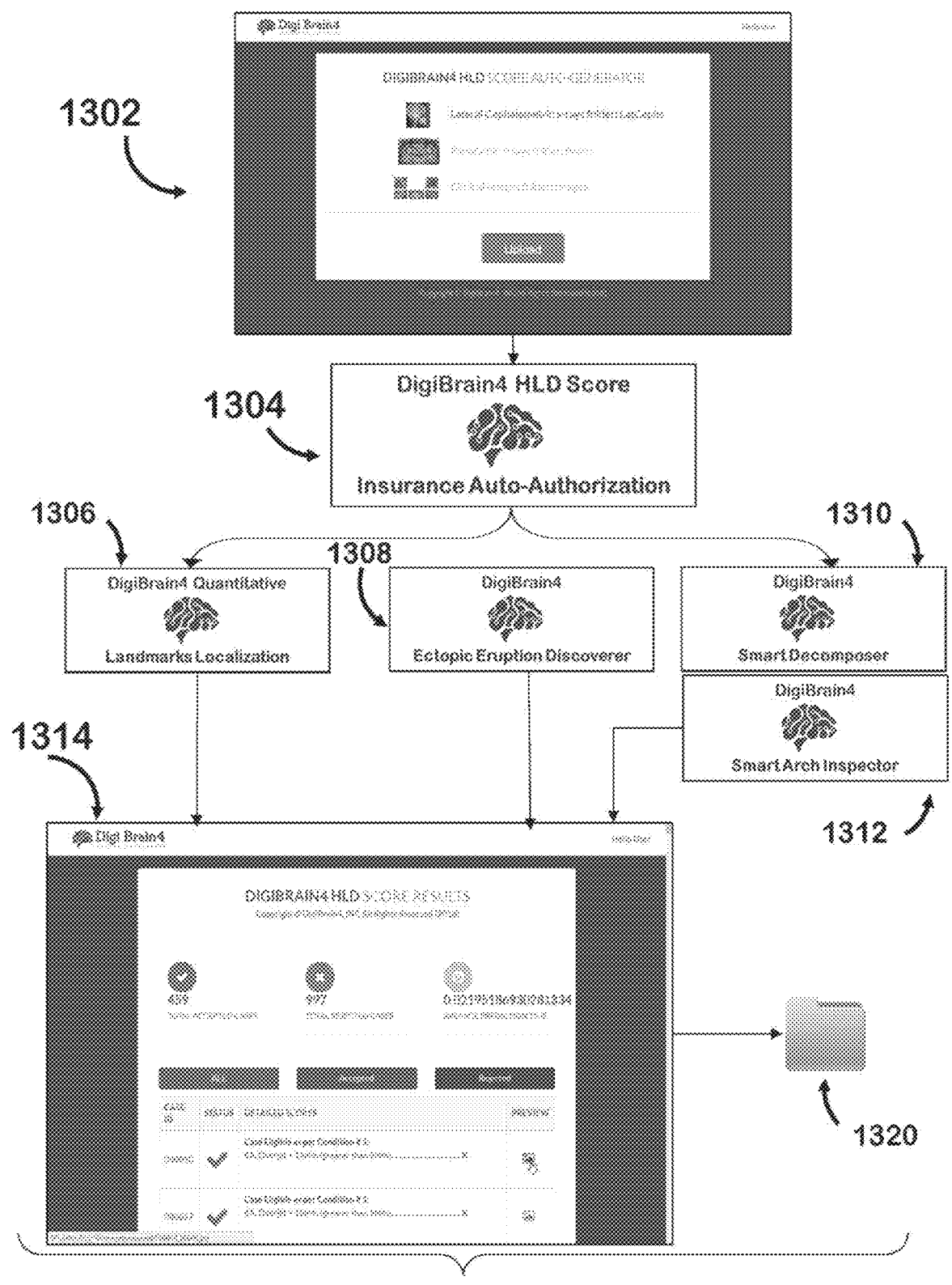
FIG. 13 illustrates one embodiment of a block diagram describing dental insurance treatment authorizer process, all tasks, and input/output data of the present system and method.

FIG. 13 is a block diagram of the process implemented by the dental insurance treatment authorizer. Two modes of input 1302, 1303 are provided to upload the required DCVA, (1) a single case-by-case web or desktop page 1302 for the user to upload single case assets, or (2) a batch mode where the user can upload all DCVA relative to any number of patient cases. The remaining tasks of the process are the same. The only difference is that for mode (1) results for a single patient is returned, in contrast for mode (2) the results for the full batch of patients will be returned.

The dental insurance treatment authorizer 1304 will recognize each asset type, category and class automatically and may then direct each asset type to the proper present system and method AI engines: (1) the landmarks localizer 1306, (2) the ectopic eruption discoverer 1308 and (3) the smart arch inspector 1310 (not disclosed in the current document). Blocks 1306 and 1308 will be detailed later, in the present system and method.

In an embodiment, the AI engines 1306, 1308 and 1310, may work in parallel and each will produce its own results. All results are then consolidated in a single report 14314, detailing the authorization status. Another summary report may also be generated as depicted in FIG. 13, box 1314. Reports for each patient, in addition to the summary reports, may all be saved in a computer file in a selected location 1320.

Figure 14:
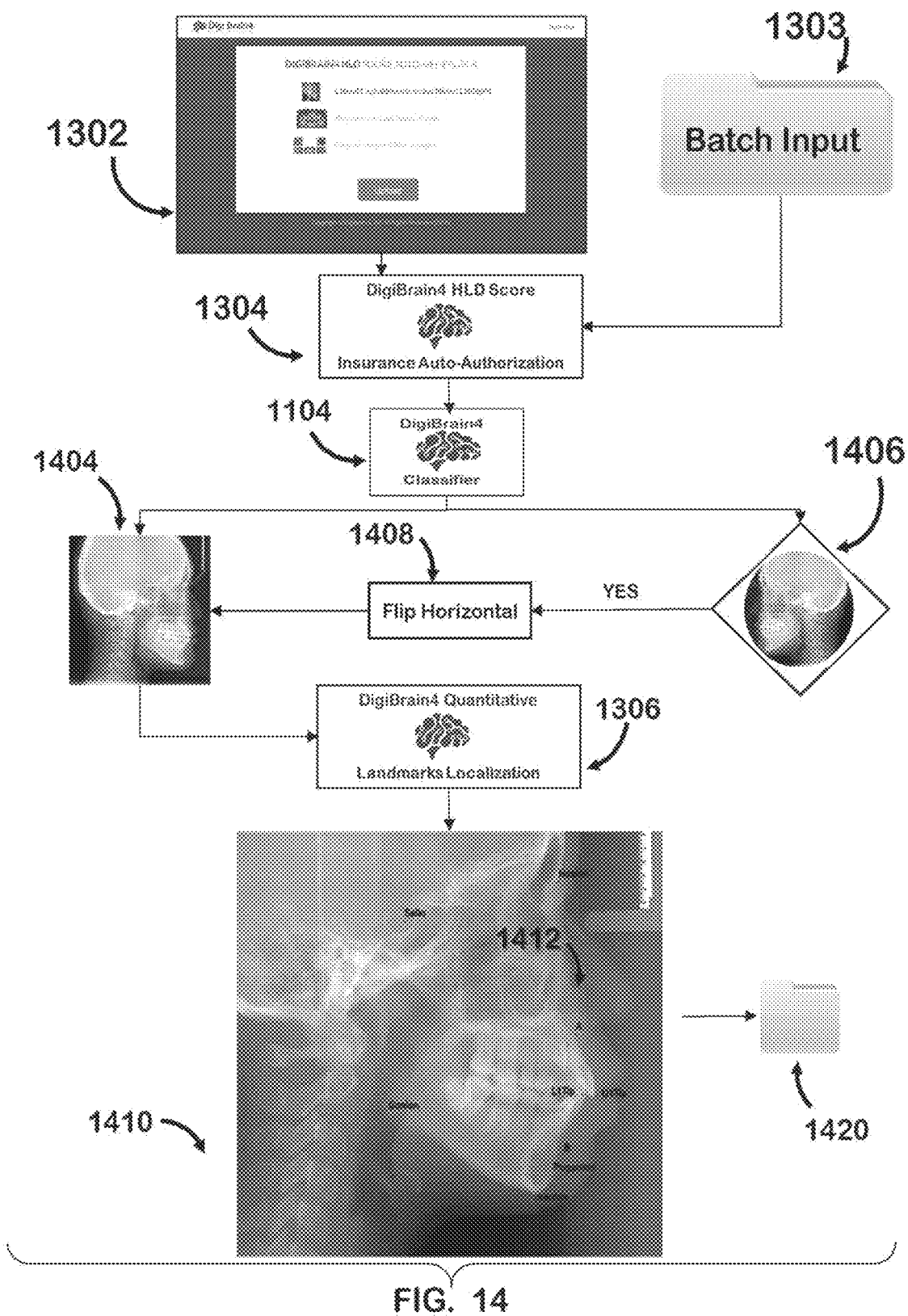
FIG. 14 illustrates one embodiment of a block diagram describing landmarks localizer process, tasks, and input/output data of the present system and method.

Referring now to FIG. 14, in an embodiment FIG. 14 may be a block diagram depicting the process and tasks of the Landmarks Localizer engine 1306 of the present system and method. The Landmark Localizer engine 1306 may accept both single lateral cephalometric x-ray 1302 and a batch 1303 of any number of lateral cephalometric x-rays.

The Classifier portion 1104 of the present system and method may recognize and discover the lateral cephalometric x-ray orientation. Right side lateral cephalometric x-rays 1404 will be accepted without modification. Left side lateral cephalometric x-rays 1406 may be horizontally auto-flipped 1408 to the standard right side view 1404, using common image processing techniques.

The proper right side lateral cephalometric x-rays 1404 may then be fed to the localizer 1306 AI engine, which may then scan the full x-ray, recognizing and localizing the required landmarks 1410 for dental insurance treatment authorization. Localized Landmarks are then drawn 1412 and overlaid on a copy of the original x-ray.

The localized landmarks will be used to calculate in millimeters: (1) Inter-incisal angle, (2) Overjet, (3) Overbite, (3) Cross bite, (4) Anterior teeth inclination, (5) Lower incisors inclination relative to the mandibular plane, (5) 7 degrees Frankfurt horizontal, (8) Mandibular angle, (9) Maxillary and Mandibular protrusion/retrusion.

Results for each x-ray are generated and saved in the proper location 1420, with patient identification along with overlaid x-rays copies.

Figure 15:
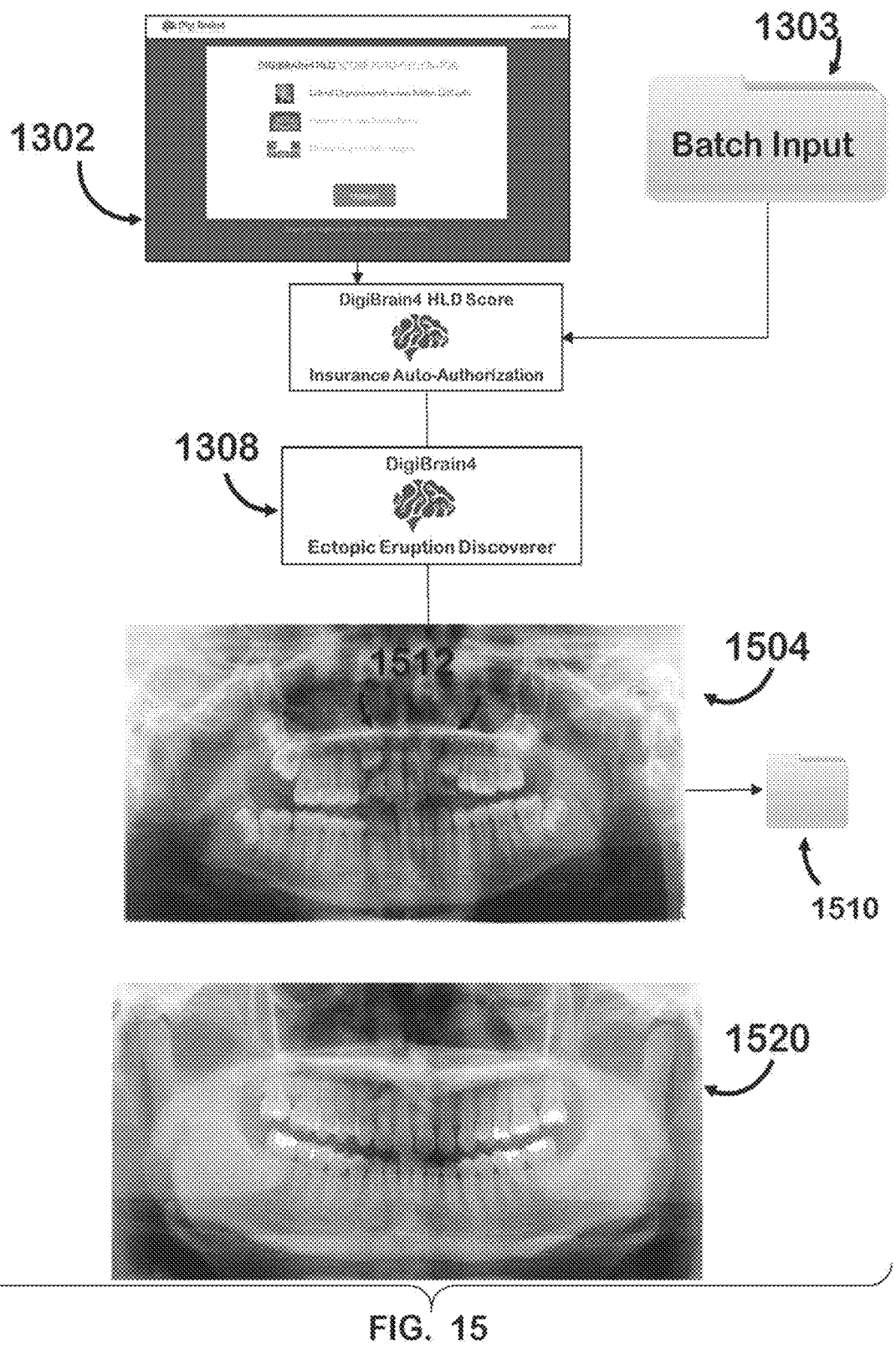
FIG. 15 illustrates one embodiment of a block diagram describing ectopic eruption discoverer process, tasks, and input/output data of the present system and method.

FIG. 15 is a block diagram depicting the process and tasks of the Ectopic Eruption Discoverer 1308 of the present system and method. As the other engines cited above, the Ectopic Eruption Discoverer 1308 may accept both single panoramic x-ray 1302 and a batch 1303 of any number of panoramic x-rays.

In an embodiment, the present Ectopic Eruption Discoverer 1308 portion of the present system and method may then scan the full x-ray, localizing the areas elected to have any of the conditions: (1) Ectopic Eruption, (2) Impacted teeth and (3) Mixed dentition cases.

The Ectopic Eruption Discoverer 1308 may then draw the discovered anomalies and overlay the drawings 1512 on a copy of the original x-ray. Results for each x-ray are generated and saved in the proper location 1510, with patient identification along with overlaid x-rays copies. Ectopic Eruption Discoverer 1308 may then correctly interpret normal panoramic x-rays without searched-for anomalies and will not annotate those 1520.

Figure 16:
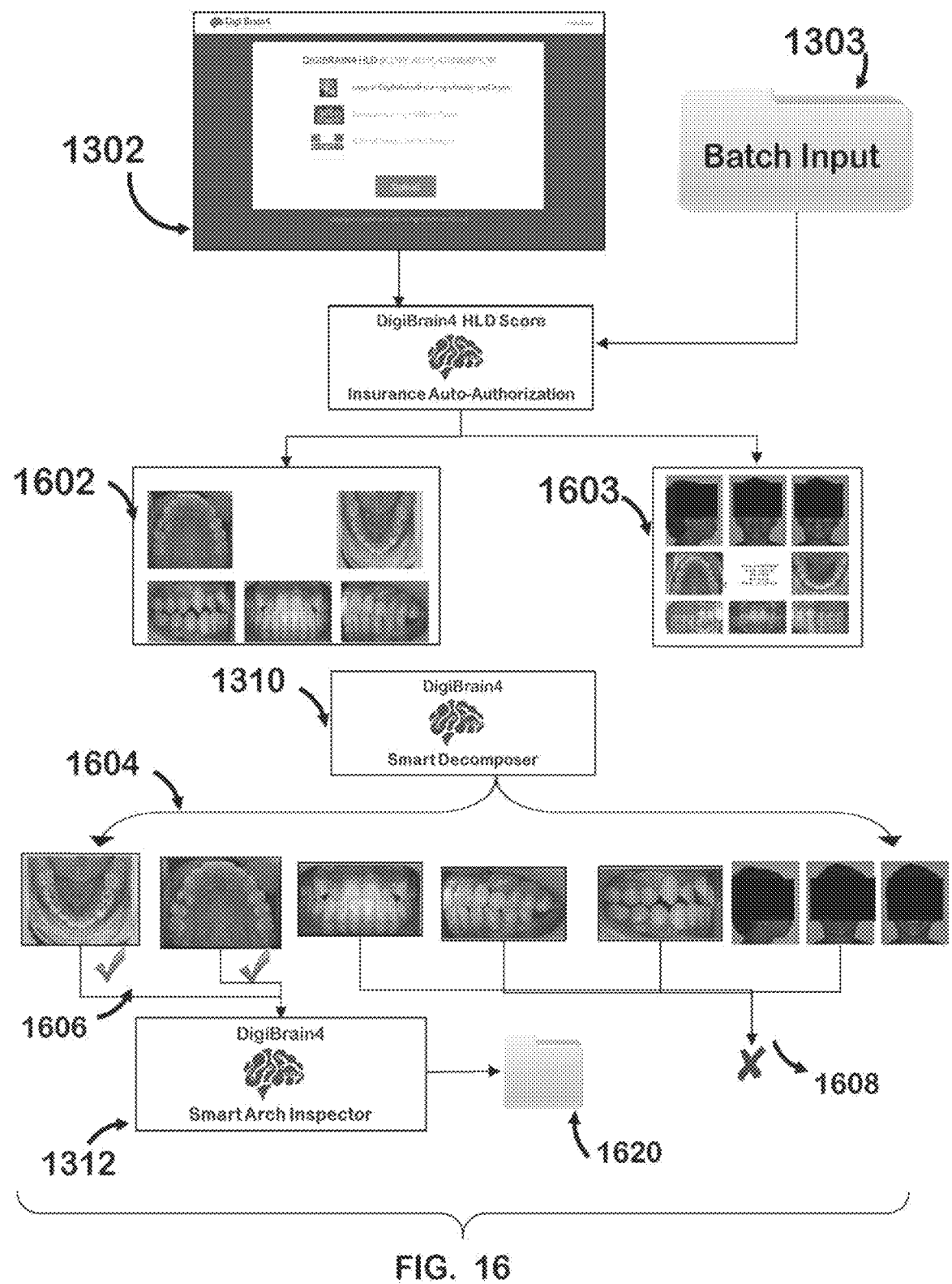
FIG. 16 illustrates one embodiment of a block diagram describing the smart decomposer process, tasks, and input/output data of the present system and method.

FIG. 16 is a block diagram for the Smart Decomposer 1301 process of the present system and method. The Smart Decomposer 1301 may accept both (1) single patient composite image and (2) batch of composite images of any number. The composite images may recognize and decompose both: (1) Five image views 1602 and (2) Eight image views 1603. Eight image composites may or may not contain textual patient demographic data. Regardless of the composite type, component images will be recognized, decomposed and saved as individual image files 1604.

Figure 17:
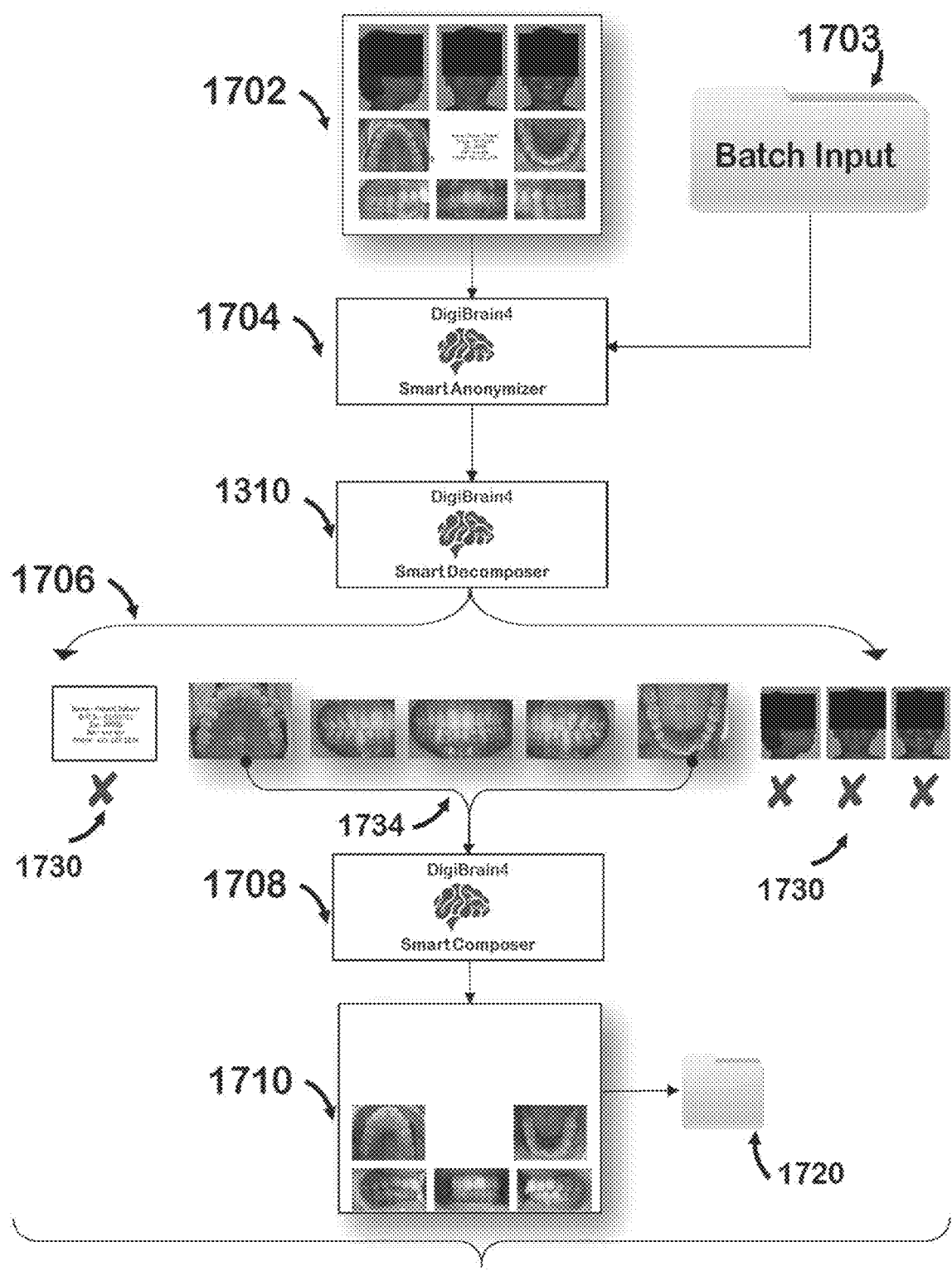
FIG. 17 illustrates one embodiment of a block diagram describing the smart composer and smart anonymizer processes, tasks, and input/output data of the present system and method.

FIG. 17 is a block diagram for the Smart Composer and Smart Anonymizer portion of the present system and method. Both the Smart Composer and Smart Anonymizer portion may accept single 1702 and batch 1703 composite images. The decomposer may recognize and decompose the image, through Classifier 1104 portion of the present system and method, into its constituent's views 1706. Non-relevant assets 1730 may then be discarded, and only the proper views 1734 will be selected, including textual demographics.

The Smart Composer 1708 may then collect the properly identified image views, through present system and method Classifier 1104, and create a new composite image 1710 showing only the required image views in the proper places. The Smart Composer 1708 may then save the newly created composites 1710 in the selected location 1720.

While the embodiments have been illustrated and described in detail in the drawings and foregoing description, the same should be considered as illustrative and not restrictive in character. It is understood that only the preferred embodiments have been presented and that all changes, modifications and further applications that come within the spirit of the invention are desired to be protected.

REFERENCES

[1] David Daniel Cox and Thomas Dean, "Neural Networks and Neuroscience-Inspired Computer Vision", Current Biology 24, R921-R929, Sep. 22, 2014, 2014 Elsevier Ltd All rights reserved http://dx.doi.org/10.1016/j.cub.2014.08.026.

[2] Dominik Scherer, Andreas Muller, and Sven Behnke, University of Bonn, Institute of Computer Science VI, Autonomous Intelligent Systems Group, Romerstr. 164, 53117 Bonn, Germany, "Evaluation of Pooling Operations in Convolutional Architectures for Object Recognition", 20th International Conference on Artificial Neural Networks (ICANN), Thessaloniki, Greece, September 2010.

[3] Christian Szegedy, Google Inc., Wei Liu, University of North Carolina, Chapel Hill, Yangqing Jia, Google Inc., Pierre Sermanet, Google Inc., Scott Reed, University of Michigan, Dragomir Anguelov, Google Inc., Dumitru Erhan, Google Inc., Vincent Vanhoucke, Google Inc., Andrew Rabinovich, Google Inc., "Going deeper with convolutions", arXiv:1409.4842v1 [ cs.CV] 17 Sep. 2014.

[4] Min Linl, Qiang Chen, Shuicheng Yan, Graduate School for Integrative Sciences and Engineering, Department of Electronic & Computer Engineering, "Network In Network", arXiv:1312.4400v3 [cs.NE] 4 Mar. 2014.

[5] Forrest N. Iandolal, Song Han, Matthew W. Moskewicz, Khalid Ashraf, William J. Dally, Kurt Keutzer. DeepScale & UC Berkeley, Stanford University, "Squeezenet: Alexnet-Level Accuracy With 50× Fewer Parameters And <0.5 mb Model Size", arXiv: 1602.07360v4 [cs.CV] 4 Nov. 2016.

[6] Lin T-Y, Maire M, Belongie S, Hays J, Perona P, Ramanan D, et al., editors. Microsoft COCO: Common Objects in Context 2014; Cham: Springer International Publishing.

[7] Joseph Redmon, Santosh Divvala, Ross Girshick, Ali Farhadi, University of Washington, Allen Institute for AI, Facebook AI Research: You Only Look Once Unified Real Time Object Detection, arXiv:1506.02640v5 [cs.CV] 9 May 2016.

We claim:

1. A method for automatically recognizing, classifying and processing dento-craniofacial visual assets by a processor-based machine using machine learning steps to provide results for treatment of a patient in a report, comprising:
    receiving dento-craniofacial visual asset images from a machine;
    inserting the visual asset images obtained by the machine into a search engine of the processor-based machine wherein the search engine uses a nueral network learning computer program having dento-craniofacial asset data and terminology and wherein the processor-based machine recognizes, classifies and labels each of the visual asset images;
    wherein the processor-based machine rejects non-dentocranofacial images;
    wherein the processor-based machine uses the nueral network learning computer program to produce a numeric score index of the inserted visual asset;
    providing a report for a treatment analysis based on the numeric score index produced by the processor-based machine;
    wherein the report is saved in an electrical digital format.

2. The method of claim 1 wherein the method is capable of recognizing, classifying and labeling the dento-craniofacial visual assets as one of:
    i) radiographs, clinical images, or miscellaneous visual assets; and further one of:
    ii) intra-oral radiographs, extra-oral radiographs, intra-oral clinical images, or an extra-oral clinical image; and further one of:
    iii) a panoramic x-ray, left cephalometric x-ray, right cephalometric x-ray, upper periapical x-ray, lower periapical x-ray, bitewing x-ray, upper arch occlusal x-ray, lower arch occlusal x-ray, right patient profile, facial profile, facial profile smiling, left occlusal clinical images, right occlusal clinical images, front occlusal clinical images, upper arch clinical image, lower arch clinical image or miscellaneous visual asset image.

3. The method of claim 1 further comprising the step of:
    discriminating dental from non-dento-craniofacial visual asset image; and
    recognizing and rejecting all non-relevant assets during the recognizing and classification.

4. The method of claim 1 further comprising the step of:
    creating metadata from the processor-based machine and saving all created metadata, including saving a comma separated value, a relational database and a NoSQL database wherein the saved metadata is used to respond to a complex query and a pattern match.

5. A deep learning method for searching visual big-data and generating a report for analysis, comprising the step of:
    searching a dento-craniofacial visual asset repository using accepted dental terminology to return only a searched for visual asset;
    discriminating between an upper arch and a lower arch and teeth assets using a nueral network learning computer program trained on a prior submitted upper arch and lower arch and teeth and clinical assest images;
    discriminating between a right side visual asset and a left side visual asset and upper arch and a lower arch and teeth assets; and
    providing a report for finding, a score index and a treatment analysis based on results obtained from the nueral network learning computer program.

6. The deep learning method for searching visual big-data and generating a report for analysis of claim 5, further comprising the step of:
    enhancing or boosting a generic web search engine search: and
    transparently submitting a searched phrase or term inserted into the generic web search engine and then filtering any returned results to eliminate all assets non-relevant to the search phrase or term.

7. The deep learning method for searching visual big-data and generating a report for analysis of claim 5, further comprising the step of:
    anonymizing of dento-craniofacial visual asset by removing all textual demographics and facial identifiers incidences.

8. The deep learning method for searching visual big-data and generating a report for analysis of claim 5, further comprising the step of:
    generating an auto-authorization report for a dental insurance company by auto-generating a detailed quantitative and qualitative dental indices score report based on auto-analysis of extra and intra oral radiographs and clinical images.

9. The deep learning method for searching visual big-data and generating a report for analysis of claim 5, further comprising the step of:
    detecting and localizing a cephalometric landmark and generating a required cephalometric measures in mm.

10. The deep learning method for searching visual big-data and generating a report for analysis of claim 5, further comprising the step of:
    recognizing and discovering an ectopic eruption of a tooth, an impacted tooth and a mixed dentition teeth in a panoramic x-ray.

11. A deep learning method for searching visual big-data and generating a report for analysis, comprising the step of:
    searching a dento-craniofacial visual asset repository using accepted dental terminology to return only a searched for visual asset;
    discriminating between an upper arch and a lower arch and teeth assets;
    further discriminating between a right side visual asset and a left side visual asset; and
    generating an auto-authorization report for a dental insurance company by auto-generating a detailed quantitative and qualitative Handicapping Labio-Lingual Deviation Index score index report based on auto-analysis of lateral cephalometric x-rays, panoramic x-rays and clinical images.

* * * * *